US00PP32046P2

(12) United States Plant Patent
Carter

(10) Patent No.: US PP32,046 P2
(45) Date of Patent: Aug. 4, 2020

(54) ***SALVIA* PLANT NAMED 'IGNITION FUCHSIA'**

(50) Latin Name: ***Salvia* x *jamensis***
Varietal Denomination: Ignition Fuchsia

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 16/501,782

(22) Filed: Jun. 6, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — Cochran Freund & Young LLC; James M. Weatherly

(57) ABSTRACT

A new cultivar of *Salvia* named 'Ignition Fuchsia' that is distinguishable by intense vibrant magenta colored flowers which are borne early and freely on compact plants with mid-green glossy leaves, is disclosed.

2 Drawing Sheets

Genus and species: *Salvia* x *jamensis*.
Variety denomination: 'Ignition Fuchsia'.

BACKGROUND

The present disclosure relates to a new and distinct cultivar of *Salvia* plant, also known as a sage, a perennial that is grown for use as an ornamental landscape and container plant. The new variety is known botanically as *Salvia* x *jamensis* and will be referred to hereinafter by the cultivar name 'Ignition Fuchsia'.

'Ignition Fuchsia' originated and was selected from a large population of hybrid seedlings from a *Salvia* breeding program which was started in 2009. The breeding program was conducted in a greenhouse nursery in Elk, Calif. The aim of the breeding program is to develop a uniform series of compact varieties of *Salvia* x *jamensis* each with closely similar plant habits and flowering characteristics but with distinctly different and saturated flower colors. The inventor has released two varieties to date, *Salvia* plant named 'Ignition Purple' (U.S. Plant Pat. No. 27,788), and the instant variety 'Ignition Fuchsia'.

'Ignition Fuchsia' was selected by the inventor in 2015 from seedlings which resulted from the controlled hybridization using pollen collected en masse from the inventor's collection of *Salvia* varieties which bear flowers with saturated colors. The identity of the male parent is unknown. The collected pollen was applied to the flowers of the inventor's proprietary variety *Salvia* x *jamensis* 'Elk Ruby Ruby II' (unreleased, unpatented) as female parent.

'Ignition Fuchsia' was selected for its intense vibrant deep magenta colored flowers which are borne on compact plants with mid-green glossy leaves.

'Ignition Fuchsia' was first asexually propagated in spring 2016 in a greenhouse at the inventor's nursery in Elk, Calif. using softwood tip cuttings. The inventor has confirmed that 'Ignition Fuchsia' is stable and reproduces true to type in successive generations of asexual reproduction.

SUMMARY

The following traits have been repeatedly observed and represent the distinguishing characteristics of 'Ignition Fuchsia'. 'Ignition Fuchsia' has not been tested under all possible conditions and phenotypic differences may be observed with variations in environmental, climatic, and cultural conditions, without however, any variance in genotype.

1. 'Ignition Fuchsia' exhibits a compact well-branched upright plant habit.
2. The flowers of 'Ignition Fuchsia' are intense vibrant magenta in color.
3. 'Ignition Fuchsia' grows and flowers rapidly. Flowering plants may be produced in 10 to 12 weeks from a cutting.

DESCRIPTION OF THE PHOTOGRAPHS

The accompanying color photographs illustrate the overall appearance of the new *Salvia* cultivar 'Ignition Fuchsia' showing the colors as true as it is reasonably possible to obtain in colored reproductions of this type. Photographs were taken in April, 2019 in Oxnard, Calif. from a one year old plant grown outdoors in 5 gallon container, with one pinch after initial cutting establishment and without any chemical growth regulators. Colors in the photographs may differ from the color values cited in the detailed botanical description, which more accurately describes the actual colors of the new variety 'Ignition Fuchsia'.

DESCRIPTION OF THE NEW VARIETY

Figure 1:
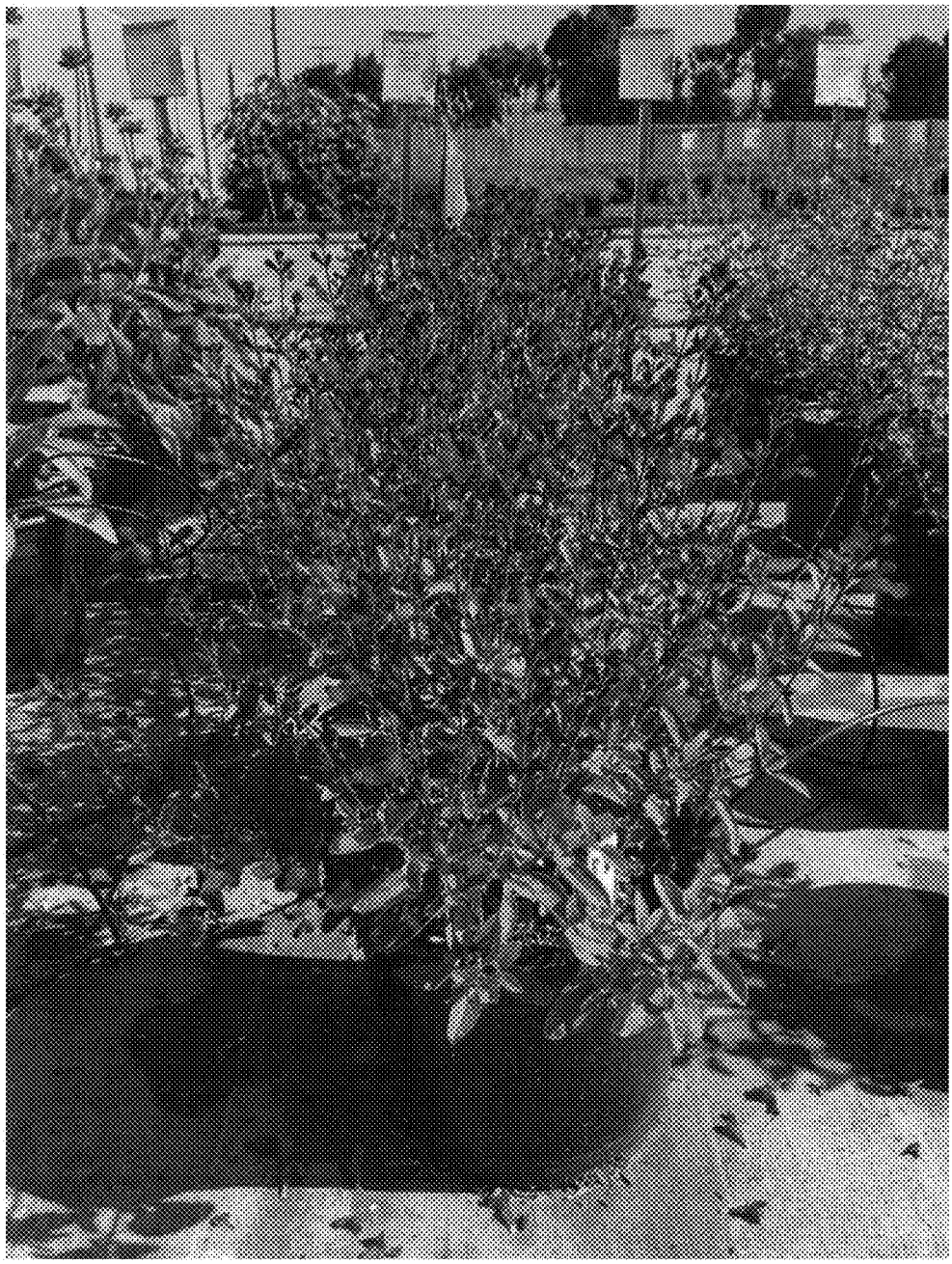
FIG. 1 depicts an entire plant in flower of 'Ignition Fuchsia'.
Figure 2:
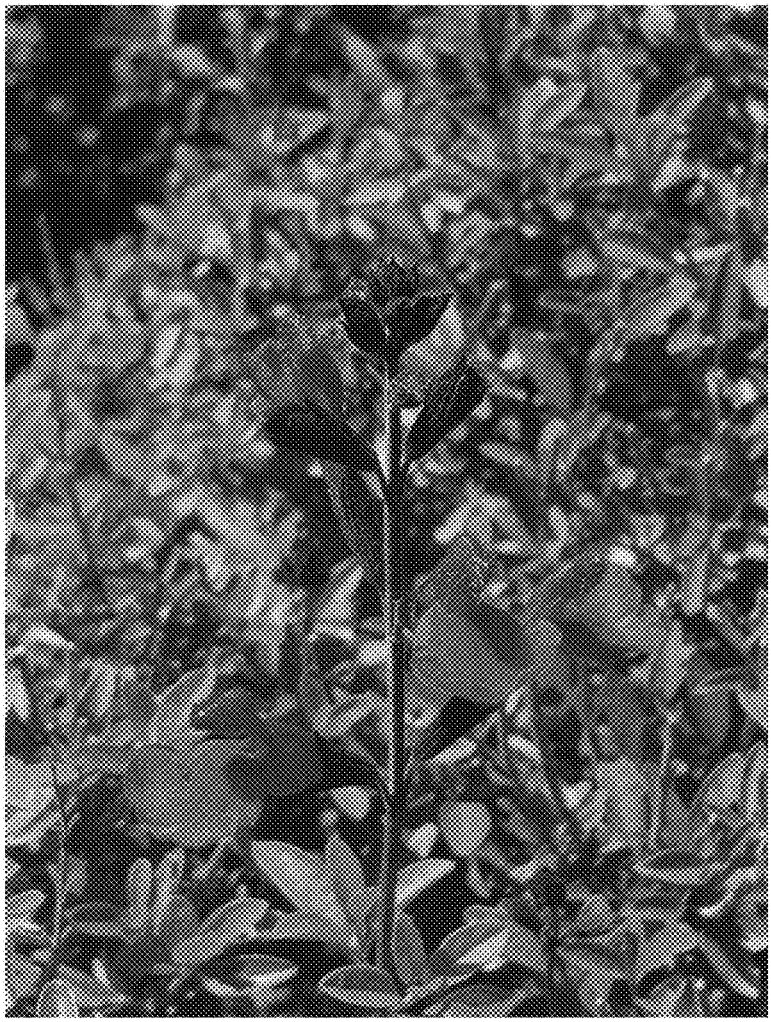
FIG. 2 depicts a close-up view of a young inflorescence of 'Ignition Fuchsia' showing its first flowers and the terminal bud cluster.

The following detailed descriptions set forth the distinctive characteristics of 'Ignition Fuchsia'. Observations, measurements, values, and comparisons were collected in May 2019 in Santa Barbara, Calif. from a one year old plant which had been growing outdoors in full sun in a 5 gallon container in Oxnard, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—x *jamensis*.

*Common name*.—Sage.

Parentage:

*Female parent*.—*Salvia* x *jamensis* 'Elk Ruby Ruby II' (unreleased, unpatented).

*Male parent*.—Unknown.

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 12 weeks are required to produce a budded and flowering plant in a quart container from a rooted cutting.

*Suggested container size*.—Quart to 1 gallon container.

*Use*.—Ornamental for use as a landscape plant or container plant.

*Type*.—Perennial.

*Overall dimensions*.—After one year's growth in a 5 gallon 40 cm in height, including the inflorescence, and 50 cm in width.

*Cultural requirements*.—Grow in full sun with moderate water and well-draining soil.

*Hardiness*.—USDA Zone 7.

*Form*.—Bush.

*Growth habit*.—Compact.

*Blooming season*.—From one month after breaking spring dormancy to first frost.

*Lastingness of blooms*.—Inflorescence has some flower for 14 days, individual flowers last for 2 to 3 days.

Stems (below first pinch):

*Condition*.—Lignified on a one-year old plant.

*Length*.—1 cm to 2 cm.

*Diameter*.—4 mm.

*Color*.—200B.

*Shape*.—Square, edges rounded.

*Texture*.—Rough.

Branches:

*Quantity*.—8 to 12.

*Shape*.—Square.

*Length*.—15 cm to 20 cm measured to base of inflorescence.

*Width*.—1.5 mm to 2.0 mm.

*Internode length*.—2 cm to 4 cm.

*Color*.—59A close to stem, becoming green 138A to 138B towards inflorescence.

Leaves:

*Type, arrangement*.—Simple, opposite.

*Attachment*.—Petiolate.

*Quantity per branch*.—8 to 10 pairs.

*Shape*.—Elliptic.

*Length*.—18 mm to 30 mm.

*Width*.—10 mm to 18 mm.

*Margin*.—Weakly undulating, shallowly crenulate, entire towards base.

*Thickness*.—Slightly fleshy.

*Venation*.—Pinnate, midrib slightly sulcate.

*Variegation*.—Absent.

*Texture*.—Adaxial surface: Glabrous, glossy. Abaxial surface: Glabrescent.

*Color*.—Adaxial surface: 143C. Abaxial surface: 138A.

*Apex*.—Acute.

*Base*.—Cuneate.

*Fragrance*.—Pleasant sage fragrance when rubbed.

*Stipules*.—Present in one or two pairs at each leaf axil; Small, sessile, elliptic, 8 mm to 10 mm in length, 4 mm to 5 mm in width; All other characteristics same as leaves.

Petiole:

*Shape*.—Terete.

*Length*.—5 mm to 11 mm.

*Width*.—1 mm.

*Texture*.—Puberulent.

*Color*.—138A.

Peduncle:

*Length*.—10 mm to 15 mm.

*Shape*.—Square.

*Width*.—1.0 mm to 1.2 mm.

*Texture*.—Puberulent.

*Color*.—Predominantly N186B, longitudinal striations of 138B.

Inflorescence:

*Type*.—Terminal raceme; two florets per inflorescence node; florets outward facing, 90-120 degrees apart.

*Length*.—8 cm to 10 cm.

*Diameter*.—5 cm.

Pedicel:

*Length*.—5 mm.

*Width*.—0.8 mm.

*Texture*.—Puberulent.

*Color*.—N186B.

Calyx:

*Shape*.—Campanulate, flared toward the apex.

*Length*.—10 mm to 12 mm.

*Height*.—4 mm.

*Width*.—12 mm across flared apex.

Sepals:

*Quantity*.—2, one upper, one lower, substantially longitudinally fused.

*Length*.—10 mm to 12 mm.

*Width*.—6 mm when flattened.

*Shape*.—Boat shaped.

*Apex*.—Acuminate.

*Base*.—Truncate.

*Margin*.—Entire.

*Texture*.—Adaxial surface: Puberulent, longitudinally ribbed; ribs 1 mm apart, raised less than 0.1 mm. Abaxial surface: Glabrous, longitudinal depressions.

*Color*.—Adaxial surface: N186B. Abaxial surface: 152B, longitudinal ribs N186B.

Flowers:

*Quantity*.—8 to 10 opposite pairs.

*Shape*.—Tubular, two-lipped.

*Fragrance*.—Pleasant sage fragrance.

Bud:

*Shape*.—Ellipsoidal.

*Length*.—4 mm to 5 mm.

*Width.*—3 mm to 4 mm.

*Texture.*—Pubescent, especially apex.

*Color.*—N79A.

Corolla:

*Shape.*—Tubular proximally to two-lipped distally, lower lip attitude relative to corolla is downward.

*Length.*—1.8 cm, including corolla tube, length 4 mm.

*Width.*—3 mm.

*Texture.*—Glossy, glandular.

*Color* (*both surfaces*).—61B, except tube base NN155B, translucent.

Petals:

*Quantity.*—2.

*Arrangement.*—One upper petal and one lower petal which appears as a large prominent lip with two lateral lobes fused to the lip and to each other.

*Upper petal.*—Shape: Hooded. Length: 10 mm. Width: 4 mm. Texture: Adaxial surface: Puberulent. Abaxial surface: Glabrous, with one longitudinal central rib. Apex: Rounded, with cluster of fine hairs approximately 1 mm in length, hair color 59A. Base: Truncate with lower lip at corolla mouth. Margin: Smooth, entire. Color: Adaxial surface: 61B. Abaxial surface: 61B, except central rib and margin 59A.

*Lower petal, lip.*—Shape: Rhomboid, concave. Length: 18 mm including lateral lobes. Width: 14 mm to 16 mm. Texture: Adaxial surface: Smooth. Abaxial surface: Smooth, glabrous, semi-glossy. Apex: Emarginate, depth of notch 2 mm. Base: Truncate. Margin: Entire, gently undulating. Color (both surfaces): 61B, adaxial surface iridescent.

*Lower petal, lateral lobes.*—Shape: Elliptic, fused at base, the pair appear as wings. Length (each lateral lobe): 6 mm. Width: 3 mm to 4 mm. Texture: Adaxial surface: Smooth. Abaxial surface: Smooth, glabrous, semi-glossy. Apex: Rounded. Base: Truncate, tiny hairs clustered towards and at the base. Margin: Smooth, entire except for hairs at the base. Color (both surfaces): 61B, adaxial surface iridescent.

*Floral bracts.*—Absent.

Reproductive organs:

*Stamens.*—Quantity: 1, comprised of two connected filaments, fused at base and longitudinally. Length: 15 mm. Color: 85C.

*Filament.*—Length: 9 mm, each filament fused for 6 mm and free for 8 mm. Color: 85C.

*Anther.*—Length: 2 mm. Width: 0.5 mm. Color: 85C.

*Pollen.*—Amount: Moderate. Color: 21B.

*Pistil.*—Quantity: 1. Stigma: Shape: Asymmetrically forked. Length: Longer fork 5 mm, strongly recurved; shorter fork 2 mm, gently recurved. Width: 0.5 mm. Color: 85C, forks N80C. Style: Length: 25 mm. Color: 85C.

*Ovary* (*only observed unfertilized*).—Length: 3 mm. Width: 1.5 mm. Color: 1B.

Seed: Rarely observed. Where present, one or two seeds per flower pollinated. Shape is ovoid, length 2 mm to 3 mm, diameter 1.5 mm. Color is black 203A. Surface is smooth and matte.

Disease and pest susceptibility: Susceptible to aphids (*Aphis gossypii*) when stressed. Generally outgrows most bacterial and viral infections. Resistant to deer and rabbit grazing.

Drought tolerance: Drought tolerant.

COMPARISON WITH PARENTAL LINES AND KNOWN VARIETY

In comparison with the female parent, 'Elk Ruby Ruby II', 'Ignition Fuchsia' grows with a more compact habit and exhibits prolific flowering and repeat flowering through the year. In addition, the flowers of 'Ignition Fuchsia' are smaller than the flowers of the female parent and are also bright magenta in color compared with darker ruby in color. Although the identity of the male parent is unknown, none of the assembled pollen donor varieties exhibited the characteristic intense magenta color of the flowers of 'Ignition Fuchsia'.

'Ignition Fuchsia' is closest in overall characteristics to the inventor's variety 'Ignition Purple' (U.S. Plant Pat. No. 27,788). The most significant difference is in flower color as between intense magenta and intense purple. In addition, the leaves of 'Ignition Fuchsia' are slightly more glossy than the leaves of 'Ignition Purple', and plants of 'Ignition Fuchsia' develop lignified stems from an earlier stage of growth.

I claim:

1. A new and distinct cultivar of *Salvia* plant named 'Ignition Fuchsia' as described and illustrated herein.

* * * * *